United States Patent [19]
Letton et al.

[11] Patent Number: 6,077,556
[45] Date of Patent: *Jun. 20, 2000

[54] SOLID, NONDIGESTIBLE, FAT-LIKE COMPOUNDS

[75] Inventors: James Carey Letton, Forest Park, Ohio; Robert David Feeney, Hackettstown, N.J.

[73] Assignee: The Procter & Gamble Company, Cincinnati, Ohio

[*] Notice: This patent is subject to a terminal disclaimer.

[21] Appl. No.: 07/941,845

[22] Filed: Sep. 8, 1992

Related U.S. Application Data

[63] Continuation of application No. 07/709,074, May 30, 1991, abandoned, which is a continuation of application No. 07/417,385, Oct. 5, 1989, abandoned, which is a continuation-in-part of application No. 07/036,738, Apr. 10, 1989, abandoned.

[51] Int. Cl.⁷ ............................. A21D 10/00; C07H 11/00
[52] U.S. Cl. .......................... 426/549; 426/601; 536/115; 536/119
[58] Field of Search ...................... 536/115, 119; 426/549, 601

[56] References Cited

U.S. PATENT DOCUMENTS

| | | | |
|---|---|---|---|
| 2,999,023 | 9/1961 | Babayan et al. | 99/180 |
| 3,093,481 | 6/1963 | Eckey et al. | |
| 3,158,490 | 11/1964 | Baur et al. | 99/118 |
| 3,249,600 | 5/1966 | Nobile et al. | 260/234 |
| 3,344,796 | 10/1967 | Yamaji et al. | 131/267 |
| 3,353,966 | 11/1967 | Hugenberg-Lutton | 99/163 |
| 3,600,186 | 8/1971 | Mattson et al. | 99/1 |
| 4,005,195 | 1/1977 | Jandacek | 424/180 |
| 4,241,054 | 12/1980 | Volpenhein | 424/180 |
| 4,611,055 | 9/1986 | Yamamoto | 536/119 |
| 4,797,300 | 1/1989 | Jandacek-Letton | 426/549 |
| 4,810,516 | 3/1989 | Kong-Chan | 426/528 |
| 4,822,875 | 4/1989 | McCoy et al. | 536/119 |

FOREIGN PATENT DOCUMENTS

| | | |
|---|---|---|
| 233856 | 8/1987 | European Pat. Off. . |
| 236288 | 9/1987 | European Pat. Off. . |
| 291106 | 11/1988 | European Pat. Off. . |
| 311154 | 4/1989 | European Pat. Off. . |
| 227137 | 9/1985 | Germany . |
| 228457 | 10/1985 | Germany . |
| 5227694 | 7/1977 | Japan . |
| 536219 | 3/1978 | Japan . |
| 536220 | 3/1978 | Japan . |
| 58-43744 | 3/1983 | Japan . |
| 5878531 | 5/1983 | Japan . |
| 58-165737 | 9/1983 | Japan . |
| 59-143550 | 8/1984 | Japan . |
| 49-26220 | 9/1984 | Japan . |
| 59-156242 | 9/1984 | Japan . |
| 61-14123 | 4/1986 | Japan . |

*Primary Examiner*—Elli Peselev
*Attorney, Agent, or Firm*—Karen F. Clark; Jacobus C. Rasser

[57] ABSTRACT

Fatty acid esters of sucrose wherein the fatty acid groups consist essentially of short chain fatty acid radicals containing from 2 to 10 carbon atoms and long chain fatty acid radicals containing from 20 to 24 carbon atoms in a molar ratio of short chain:long chain radicals of 3:5 to 5:3, the said esters having a degree of esterification of about 7 to 8. The compounds are useful as nondigestible substitutes for solid fats in foods.

23 Claims, No Drawings

SOLID, NONDIGESTIBLE, FAT-LIKE COMPOUNDS

CROSS REFERENCE TO RELATED APPLICATION

This is a continuation of application Ser. No. 07/417,385, filed on Oct. 5, 1989, now abandoned which is a continuation-in-part of U.S. Patent Application Ser. No. 07/036,738, filed Apr. 10, 1989, of James C. Letton and Robert D. Feeney, now abandoned.

FIELD OF THE INVENTION

The invention pertains to novel, nondigestible, solid fat-like compounds which are particularly useful as additives to liquid edible oils to form solid shortening compositions.

BACKGROUND

Conventional shortening compositions comprise a mixture of triglyceride materials which are respectively, liquids and solids at room temperature. Typically, the liquid triglyceride comprises about 85% of the shortening composition and the solid triglyceride about 15%. The compositions are prepared by hydrogenating a liquid triglyceride to the extent necessary to form the required amount of solid triglyceride within the mixture, or by hydrogenating a fraction-of triglyceride to a high degree (Iodine Value from 0 to about 20) to form a high melting solid, and then blending this with a liquid oil to form the solid shortening. In either case, the solid component traps relatively large amounts of the liquid component within its crystal structure, thereby forming a solid shortening, notwithstanding the fact that the amount of solid triglyceride in the shortening composition is relatively small. See U.S. Pat. No. 3,706,578, Bence, issued Dec. 19, 1972.

In recent years considerable attention has been focused on the amount of triglyceride fat in the diet from the standpoint of health concerns about obesity and hypercholesterolemia. Numerous patents have been directed to providing materials which have the physical and gustatory characteristics of triglyceride fats, but which are absorbed to a low extent or not at all by the body. These materials are referred to variously as noncaloric fats, pseudofats, nondigestible fats and fat substitutes. Patents pertaining to such materials include U.S. Pat. Nos. 4,582,927, Fulcher, issued Apr. 15, 1986, (fatty esters of malonic acid); 4,582,715, Volpenhein, issued Apr. 15, 1986, (alpha acetylated triglycerides); and 3,579,548, Whyte, issued May 18, 1981, (triglycerides of alpha-branched chain carboxylic acids).

One particular type of compound which has achieved considerable attention as a nondigestible fat is sucrose polyester (i.e., sucrose in which at least four of the eight hydroxyl groups are esterified with a fatty acid). U.S. Pat. Nos. 3,600,186, Mattson, issued Aug. 17, 1971; 4,368,213, Hollenbach et al. issued Jan. 11, 1983; and 4,461,782, Robbins et al. issued Jul. 24, 1984 describe the use of this material as a nondigestible fat in a variety of food compositions.

A problem associated with use of liquid nondigestible fats, i.e., those having a melting point below body temperature (about 37° C.), is an undesired "laxative" effect, which is manifested in leakage of the liquid nondigested fat through the anal sphincter. U.S. Pat. No. 4,005,195, Jandacek, issued Jan. 25, 1977, discloses the combining of higher melting fatty materials such as solid triglycerides and solid sucrose polyesters with the liquid sucrose polyesters in order to avoid the laxative effect.

An object of the present invention is to provide novel solid nondigestible materials which are suitable substitutes for solid fat in foods.

Other objects of the present invention are to provide improved solid nondigestible fat materials which are useful in formulating solid shortenings from liquid edible oils, and to provide materials which can be formulated into food products with liquid nondigestible oils to prevent anal leakage caused by ingestion of the products containing such oils.

For purposes of describing this invention, the term "nondigestible" shall mean being absorbable to an extent of only 70% or less (especially 20% or less) by the human body through its digestive system.

All percentages and proportions herein are "by weight" unless otherwise specified.

SUMMARY OF THE INVENTION

The invention is directed to novel solid sucrose polyesters wherein the ester groups consist essentially of a mixture of short chain saturated fatty acid radicals ($C_2$–$C_{12}$) and long chain saturated fatty acid radicals ($C_{20}$–$C_{24}$) in a molar ratio of short chain to long chain acid radicals of from about 3:5 to 5:3 (preferably 2:6 to 4:4 or 3:5 to 4:4), and wherein the degree of esterification is from about 7 to about 8.

DETAILED DESCRIPTION OF THE INVENTION

It has now been found that certain sucrose polyesters (SPE's) which are solid at temperatures of about 40° C. and higher, in addition to being suitable nondigestible substitutes for solid fat in the diet, have the ability to bind high levels of edible triglyceride oils and nondigestible oils such as liquid sucrose polyesters so as to form solid plastic compositions containing a high proportion of oil. Further, this high capacity to bind liquid oils makes these compounds particularly useful in the formulation of food products containing the nondigestible oils so as to prevent the anal leakage problem associated with the ingestion of such oils.

The novel solid compounds of the present invention are polyesters of sucrose wherein the ester groups are a combination of certain short chain and long chain saturated, straight chain fatty acid radicals. The short chain fatty acid radicals contain from 2 to about 12 carbon atoms (preferably about 6 to about 12, more preferably 6 to 10) and the long chain radicals contain from about 20 to about 24 (preferably 22) carbon atoms. The molar ratio of short chain to long chain acid radicals in the polyester molecule is from about 3:5 to 5:3 (preferably 2:6 to 4:4 or 3:5 to 4:4), and the average degree of esterification is from about 7 to about 8, i.e., from about 7 to all 8 of the hydroxyl groups of sucrose are esterified.

Examples of short chain fatty acid radicals for use in the compounds of the invention are acetate, butyrate, hexanoate (caproate), octanoate (caprylate), decanoate (caprate), and dodecanoate (laurate). Examples of suitable long chain fatty acid radicals are eicosanoate (arachidoate), docosanoate (behenate), and tetracosanate (lignocerate). Of course the short chain fatty acid radicals can be used singly or in mixtures with each other, as is also the case with the long chain acid radicals. Mixed fatty acid radicals from oils which predominate in the desired short chain or long chain saturated acids can be used as the fatty acid radicals to prepare compounds of the invention. For example, palm kernel fatty acids can be used instead of a mixture of $C_8$ to $C_{12}$ acids and hardened (i.e. hydrogenated) rapeseed oil can be used in place of a mixture of $C_{20}$ to $C_{24}$ acids. The preferred short chain fatty acid radical is caprylate and the preferred long chain fatty acid radical is behenate. The preferred ratio of short chain fatty acid to long chain fatty acid is 3:5 and it is preferred that all of the hydroxyl groups of sucrose be esterified, i.e., that the compound be the octaester. The most preferred compound of the invention is sucrose tricaprylate pentabehenate.

The compounds of the present invention can be made according to prior known methods for preparing polyesters of sucrose. One such method is by reacting the acid chlorides of the fatty acids with sucrose. In this method a mixture of the long and short chain acid chlorides can be reacted in one step with sucrose or the long and short chain acid chlorides can be reacted sequentially with sucrose. Another preparation method is by the process of reacting methyl esters of the fatty acids with sucrose in the presence of a fatty acid soap and a basic catalyst such as potassium carbonate. See, for example, U.S. Pat. Nos. 3,963,699, Rizzi et al., issued Jun. 15, 1976; 4,518,772, Volpenhein, issued May 21, 1985; and 4,517,360, Volpenhein, issued May 14, 1985, all incorporated herein by reference. When using the methyl ester route for preparing the compounds herein, the octaester of the short chain fatty acid can be prepared first, then this product is partially interesterified with the methyl ester of the long chain fatty acid in order to obtain the sucrose ester of mixed short chain/long chain fatty acids. In a preferred way of practicing the methyl ester process, the long chain methyl esters are reacted with sucrose in a first stage at about 135° C. to obtain the partial esters of sucrose and the long chain acid. The short chain methyl esters are then added to the reaction and the temperature is dropped to 90°–120° C., as necessary, and reflux is maintained by adjusting pressure and/or temperature to keep the short chain methyl esters in the reactor. Reflux is maintained until the desired degree of esterification has been attained.

The solid SPE compounds of the present invention are all solids at temperatures below about 40° C. They have the ability to trap large amounts of oil within their crystal structure, and as a consequence, can be blended in relatively small amounts (on the order of about 10% to 20%) with liquid oils to convert the oils to solid, gel-like compositions, i.e., compositions which remain in a solid gel state at temperatures below about 40° C. The oils can be conventional digestible triglyceride oils such as cottonseed and corn oils, or nondigestible, edible oils.

Some of the solid SPE compounds of the invention exhibit a beta prime-like crystal structure which is characteristic of triglycerides. However, not all compounds of the invention exhibit this structure and, therefore, it is not a required characteristic of compounds of the invention.

Examples of nondigestible edible oils are liquid polyesters of sugars and sugar alcohols (U.S. Pat. No. 4,005,195, Jandacek, issued Jan. 25, 1977); liquid esters of tricarballytic acids (U.S. Pat. No. 4,508,746, Hamm, issued Apr. 2, 1985); liquid diesters of dicarboxylic acids such as malonic and succinic acid (U.S. Pat. No. 4,582,927, Fulcher, issued Apr. 15, 1986); liquid triglycerides of alpha-branched chain carboxylic acids (U.S. Pat. No. 3,579,548, Whyte, issued May 18, 1971);ethers and ether esters containing the neopentyl moiety (U.S. Pat. No. 2,962,419, Minich, issued Nov. 29, 1960; fatty polyethers of polyglycerol (U.S. Pat. No. 3,932,532, Hunter et al., issued Jan. 13, 1976); all incorporated herein by reference. A type of liquid nondigestible oil disclosed in U.S. Pat. No. 4,005,195 is a polyol fatty acid polyester having at least 4 fatty acid ester groups, wherein the polyol is selected from the group consisting of sugars and sugar alcohols containing from 4 to 8 hydroxyl groups and wherein each fatty acid group has from about 8 to 22 carbon atoms: Examples of preferred polyols for said polyesters are sugars, including monosaccarides and disaccharides, and sugar alcohols. Examples of monosaccharides containing four hydroxyl groups are xylose and arabinose and the sugar alcohol derived from xylose, which has five hydroxyl groups, i.e., xylitol. (The monosaccharide, erythrose, is not suitable in the practice of this invention since it only contains three hydroxyl groups, but the sugar alcohol derived from erythrose, i.e., erythritol, contains four hydroxyl groups and accordingly can be used.) Suitable five hydroxyl group-containing monosaccharides are galactose, fructose, and sorbose. Sugar alcohols containing six—OH groups derived from the hydrolysis products of sucrose, as well as glucose and sorbose, e.g., sorbitol, are also suitable. Examples of disaccharide polyols which can be used include maltose, lactose, and sucrose, all of which contain eight hydroxyl groups.

Preferred polyols for preparing the polyesters for use in the present invention are selected from the group consisting of erythritol, xylitol, sorbitol, glucose and sucrose. Sucrose is especially preferred.

The nondigestible solid fat materials of the present invention (or blends of said materials with liquid triglyceride oils and nondigestible edible oils), are useful in a wide variety of food and beverage products.

For example, they can be used in the production of baked goods in any form, such as mixes, shelf-stable baked goods, and frozen baked goods. Possible applications include, but are not limited to, cakes, brownies, muffins, bar cookies, wafers, biscuits, pastries, pies, pie crusts, and cookies, including sandwich cookies and chocolate chip cookies, particularly the storage-stable dual-textured cookies described in U.S. Pat. No. 4,455,333 of Hong & Brabbs. The baked goods can contain fruit, cream, or other fillings. Other baked good uses include breads and rolls, crackers, pretzels, pancakes, waffles, ice cream cones and cups, yeast-raised baked goods, pizzas and pizza crusts, and baked farinaceous snack foods, and other baked salted snacks.

In addition to their uses in baked goods, the nondigestible solid fat materials herein can be used alone or in combination with other nondigestible or zero calorie fats to make shortening and oil products. The other fats can be synthetic or derived from animal or vegetable sources, or combinations of these. Shortening and oil products include, but are not limited to, shortenings, margarines, spreads, butter blends, lards, cooking and frying oils, salad oils, popcorn oils, salad dressings, mayonnaise, and other edible oils.

The present nondigestible solid fat materials can also be fortified with vitamins and minerals, particularly the fat-soluble vitamins. The fat-soluble vitamins include vitamin A, vitamin D, vitamin E, and vitamin K. Vitamin A is a fat-soluble alcohol of the formula $C_{20}H_{29}OH$. Natural vitamin A is usually found esterified with a fatty acid; metabolically active forms of vitamin A also include the corresponding aldehyde and acid. Vitamin D is a fat-soluble vitamin well known for use in the treatment and prevention of rickets and other skeletal disorders. "Vitamin D" comprises sterols, and there are at least 11 sterols with vitamin D-type activity. Vitamin E (tocopherol) is a third fat-soluble vitamin which can be used in the present invention. Four different tocopherols have been identified (alpha, beta, gamma and delta), all of which are oily, yellow liquids, insoluble in water but soluble in fats and oils. Vitamin K exists in at least three forms, all belonging to the group of chemical compounds known as quinones. The naturally occurring fat-soluble vitamins are $K_1$ (phylloquinone), $K_2$ (menaquinone), and $K_3$ (menadione). The amount of the fat-soluble vitamins employed herein to fortify the present low calorie fat materials can vary. If desired, the fat materials can be fortified with a recommended daily allowance (RDA), or increment or multiple of an RDA, of any of the fatsoluble vitamins or combinations thereof. See U.S. Pat. No. 4,005,916, Jandacek et al., issued Jan. 25, 1977, incorporated herein by reference.

Vitamins that are nonsoluble in fat can similarly be included in the present nondigestible solid fat materials. Among these vitamins are the vitamin B complex vitamins, vitamin C, vitamin G, vitamin H, and vitamin P. The minerals include the wide variety of minerals known to be useful in the diet, such as calcium, magnesium, and zinc. Any combination of vitamins and minerals can be used in the present low-calorie fat materials.

The present nondigestible solid fat materials (or blends thereof with edible oils) are particularly useful in combination with particular classes of food and beverage ingredients. For example, an extra calorie reduction benefit is achieved when the fat materials are used with noncaloric or reduced calorie sweeteners alone or in combination with bulking agents. Noncaloric or reduced calorie sweeteners include, but are not limited to, aspartame; saccharin; alitame, thaumatin; dihydrochalcones; cyclamates; steviosides; glycyrrhizins, synthetic alkoxy aromatics, such as Dulcin and P-4000; sucralose, suosan; miraculin; monollin; sorbitol; xylitol; talin; cyclohexyl sulfamates; substituted imidazolines; synthetic sulfamic acids such as acesulfame, acesulfam-K and n-substituted sulfamic acids; oximes such as perilartine; rebaudioside-A; peptides such as aspartyl malonates and succanilic acids; dipeptides; amino acid based sweeteners such as gem-diaminoalkanes, meta-aminobenzoic acid, L-aminodicarboxylic acid alkanes, and amides of certain alpha-aminodicarboxylic acids and gem-diamines; and 3-hydroxy-4-alkyloxyphenyl aliphatic carboxylates or heterocyclic aromatic carboxylates.

The nondigestible solid fat materials herein can be used in combination with other nondigestible fats, such as branched chain fatty acid triglycerides, triglycerol ethers, polycarboxylic acid esters, sucrose polyethers, neopentyl alcohol esters, silicone oils/siloxanes, and dicarboxylic acid esters. Other partial fat replacements useful in combination with the materials herein are medium chain triglycerides, highly esterified polyglycerol esters, acetin fats, plant sterol esters, polyoxyethylene esters, jojoba esters, mono/diglycerides of fatty acids, and mono/diglycerides of short-chain dibasic acids.

Bulking or bodying agents are useful in combination with the nondigestible solid fat materials herein in many food compositions. The bulking agents can be nondigestible carbohydrates, for example, polydextrose and cellulose or cellulose derivatives, such as carboxymethylcellulose, carboxyethylcellulose, hydroxypropylcellulose, methylcellulose and microcrystalline cellulose. Other suitable bulking agents include gums (hydrocolloids), starches, dextrins, fermented whey, tofu, maltodextrins, polyols, including sugar alcohols, e.g., sorbitol and mannitol, and carbohydrates, e.g., lactose.

Similarly, food and beverage compositions can be made that combine the present nondigestible solid fat materials with dietary fibers to achieve the combined benefits of each. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and manmade fibers (for example, by bacterial synthesis). Commercial fibers such as purified plant cellulose, or cellulose flour, can also be used. Naturally occurring fibers include fiber from whole citrus peel, citrus albedo, sugar beets, citrus pulp and vesicle solids, apples, apricots, and watermelon rinds.

These dietary fibers may be in a crude or purified form. The dietary fiber used may be of a single type (e.g., cellulose), a composite dietary fiber (e.g., citrus albedo fiber containing cellulose and pectin), or some combination of fibers (e.g., cellulose and a gum). The fibers can be processed by methods known to the art.

Of course, judgment must be exercised to make use of the nondigestible solid fat materials and combinations thereof with other food ingredients. For example, a combination of sweetener and nondigestible solid fat material would not be used where the specific benefits of the two are not desired. The nondigestible solid fat materials and nondigestible solid fat material/ingredient combinations are used where appropriate, and in appropriate amounts.

Many benefits are obtained from the use of the present nondigestible solid fat materials in food and beverage compositions, either when used alone or in combination with edible oils and/or other ingredients discussed above. A primary benefit is the calorie reduction achieved when nondigestible fat materials are used as a total or partial fat replacement. This calorie reduction can be increased by using combinations of the present nondigestible solid fat materials with reduced calorie sweeteners, bulking agents, or other nondigestible fats and oils. Another benefit which follows from this use is a decrease in the total amount of fats in the diet. Foods or beverages made with the nondigestible solid fat materials instead of triglyceride fats will also contain less cholesterol, and the ingestion of these foods can lead to reduced serum cholesterol and thus reduced risk of heart disease.

A related benefit is that the use of the nondigestible solid fat materials allows the production of foods and beverages that are stable in terms of shelf stability and penetration stability. Compositions made with these fat materials have acceptable organoleptic properties, particularly taste and texture.

Dietary foods can be made with the nondigestible solid fat materials, to meet special dietary needs, for example, of persons who are obese, diabetic, or hypercholesterolemic. The nondigestible solid fat materials can be a major part of a low-fat, lowcalorie, low-cholesterol diet, and they can be used alone or in combination with drug therapy or other therapy. Combinations of food or beverage products made with the nondigestible solid fat materials can be used as part of a total dietary management regimen, based on one or more of these products, containing the fat materials alone or in combination with one or more of the above-mentioned ingredients, to provide one or more of the above-mentioned benefits.

In formulating food products comprising fat and nonfat ingredients (e.g., margarines, mayonnaise, baked goods, etc.) in which the fat component comprises a nondigestible oil (e.g., a liquid sucrose polyester such as sucrose octaoleate), the solid SPE's of the present invention can be included in said products to prevent anal leakage of the nondigestible oil which would otherwise occur as a result of ingestion of the products. The solid SPE will generally be used in the food products at a level such that the ratio of the nondigestible oil to solid SPE is from about 9:1 to about 3:1.

This discussion of the nondigestible solid fat material uses, combinations, and benefits is not intended to be limiting or allinclusive. It is contemplated that other similar uses and benefits can be found that will fall within the spirit and scope of this invention.

In addition to food compositions, the compounds of the present invention can be used in formulating lubricants, skin creams, pharmaceutical ointments, and the like.

A listing of representative solid sucrose polyesters of the present invention is shown in the following table.

TABLE 1

Solid Sucrose Polyesters

| | Short Chain Acid* | Long Chain Acid* | Ratio of Short:Long Chain** | Average Degree of Esterification | Melting Point- °C. | Hydroxyl Value |
|---|---|---|---|---|---|---|
| 1 | $C_4$ | $C_{22}$ | 4:4 | 7.99 | 49 | 0.22 |
| 2 | $C_6$ | $C_{22}$ | 4:4 | 7.97 | 44 | 0.65 |
| 3 | $C_8$ | $C_{22}$ | 4:4 | 7.88 | 48 | 3.1 |
| 4 | $C_{10}$ | $C_{22}$ | 4:4 | 7.87 | 47 | 3.2 |
| 5 | $C_8$ | $C_{24}$ | 4:4 | 7.81 | 52 | 5.5 |
| 6 | $C_2$ | $C_{22}$ | 4:4 | 7.87 | 58 | 4.2 |

*Straight chain saturated monocarboxylic acids.
**Ratio of moles of short chain:long chain acid chlorides used in the reaction to prepare the desired products.
Note:
Compounds 1 through 5 have a beta prime-like crystal structure.

The invention will be illustrated by the following examples.

EXAMPLE I

Preparation of Tetrabehenyl Tetracaprylyl Sucrose (Acid Chloride Route)

| Chemicals: | Mol. Wt. | Wt. (g) | Moles | Mole Ratio |
|---|---|---|---|---|
| A. Reaction | | | | |
| 1. Sucrose | 342.3 | 7 | 0.0204 | 1 |
| 2. Behenyl Chloride (Docosanoyl Chloride) | 358.6 | 30 | 0.0836 | 4.09 |
| 3. Caprylyl Chloride (Octanoyl Chloride) | 162 | 15 | 0.0925 | 4.53 |
| B. Solvents | | | | |
| 1. Pyridine | | | | |
| 2. Dimethylformamide | | | | |
| 3. Dichloromethane | | | | |
| 4. Methanol | | | | |

Procedure

Seven grams of sucrose (anhydrous) were dissolved by warming in a mixture of 150 ml pyridine and 75 ml of dimethylformamide (DMF). Both solvents had been dried over 4A molecular sieves.

Thirty grams of the acid chloride of behenic ($C_{22}$) acid were dissolved in 100 ml of dichloromethane and the acid chloride solution added dropwise to the sucrose solution. The reaction temperature was held at 32° C. by use of a cold water bath. Addition time was 30 minutes.

After addition of the $C_{22}$ acid chloride, the reaction mixture was warmed to 40° C., removed from the water bath and allowed to stir at ambient temperature for four additional hours.

After four hours of reaction time, 15 grams of caprylyl chloride in 50 ml of dichloromethane were added. Addition time was 30 minutes and the reaction temperature was maintained at 30–35° C. After addition of the caprylyl chloride, the reaction mixture was allowed to stir overnight.

After stirring overnight, the reaction mixture was diluted with 30 ml of methanol to convert excess acid chlorides to their methyl esters. The reaction mixture was then diluted with 300 ml of dichloromethane and combined in a separatory funnel with 300 ml of a dilute salt (NaCl) solution. The mixture was shaken then allowed to separate.

The organic (dichloromethane) layer was washed a second time with a dilute salt solution followed by washing with dilute HCl (to remove residual pyridine), then with water until the last wash was neutral to pH paper.

The dichloromethane solution was dried over anhydrous sodium sulfate then stripped under vacuum with heating to a liquid residue. The product solidified on standing. The solid product was melted in a hot water bath then extracted three times with methanol (the methanol layers were removed by decantation).

The reaction product was stripped again under vacuum and the residue dissolved in 80 ml of dichloromethane. The solution was stirred and 80 ml of methanol were slowly added to induce crystallation. The mixture was again vacuum distilled to displace the dichloromethane with additional methanol added during distillation. A white precipitate (crystalline) formed and the suspension was cooled in a water bath then filtered to give 40.5 grams of dried product.

Yield-93% of theoretical

Analytical

1. Hydroxyl value-3.1
2. Average degree of esterification-7.88 (calculated from hydroxyl value as an approximation)
3. Estimated % octaester-90.6

EXAMPLE II

Preparation of Tetrabehenyl TetracaDrylyl Sucrose (Methyl Ester Route)

An alternative method for preparation of $C_8$–$C_{22}$ sucrose polyesters is by a modification of the process described in U.S. Pat. Nos. 4,518,772, supra, and 4,517,360, supra. Sucrose is reacted with methyl caprylate in the presence of a potassium soap and a basic catalyst such as $K_2CO_3$ to form sucrose octacaprylate. The octacaprylate is then reacted with methyl behenate in the presence of sodium methoxide for an interesterification to the $C_8$–$C_{22}$ product of interest.

| Chemicals | Mol. Wt. | Wt. (g) | Moles | Mole Ratio |
|---|---|---|---|---|
| A. Reaction | | | | |
| 1. Sucrose | 342.3 | 300.00 | 0.0204 | 1 |
| 2. Potassium Behenate | 387.60 | 124.10 | 0.328 | 0.375 |

-continued

| Chemicals | Mol. Wt. | Wt. (g) | Moles | Mole Ratio |
|---|---|---|---|---|
| 3. Methyl Caprylate | 158.24 | 1663.40 | 6.132 | 7.000 |
| 4. Methyl Behenate | 354.60 | 2174.40 | 6.132 | 7.000 |
| 5. Potassium Carbonate | 138.21 | 12.107 | 0.0876 | 0.100 |
| 6. Sodium Methoxide | | 54.00 (1/2% by wt. of mixture | | |
| B. Solvents | | | | |
| 1. Methanol | | | | |
| 2. Hexane | | | | |

Procedure:

Step A—Preparation of Potassium Behenate

Methyl behenate (0.375 moles/mole of sucrose to be used in Step B) is saponified by stirring at reflux in methanol containing an equivalent amount of KOH. The reaction is stirred with heating until all methyl ester has been converted to soap as indicated by infrared analysis. The soap solution is used, as is in the next reaction step.

Step B—Preparation of Sucrose Octacaprylate

Methyl caprylate (12 moles/mole of sucrose) is added directly to the potassium behenate-methyl alcohol solution from Step A above. The mixture is stripped under vacuum to remove the methanol. Sucrose and potassium carbonate are then added to the soap-methyl caprylate mixture and the reaction mixture heated to 135° C. and placed under a partial vacuum.

The reaction is allowed to proceed until the sucrose is converted to its octacaprylate. The endpoint is determined by liquid or super critical fluid chromatography.

The reaction mixture is cooled to 95° C. and 7% $H_2O$ is added to form the hydrate of the soap.

The soap separates as a sludge and is removed by centrifugation, filtration and/or decantation. The oil layer (sucrose octacaprylate/methyl ester layer) is washed several times with hot water, separated and the residual water removed by $N_2$ sparging at 110° C.

The crude octacaprylate is then decolorized with a mixture of filtrol and celite and the bleaching earths removed by vacuum filtration. The excess methyl esters are removed by distillation at 130° C. and 1 mm Hg.

Step C—Preparation of $C_8$–$C_{22}$ Sucrose Polyesters

Sucrose octacaprylate (from Step B above) and 7 moles of methyl behenate are combined with sodium methoxide in a reactor. While stirring, the temperature is raised to 120° C. and the reactor placed under vacuum.

The methyl caprylate formed during interesterification is distilled from the reaction mixture and collected. The reaction is continued until 4–5 moles of methyl caprylate are collected (the ratio of $C_8$–$C_{22}$ on the sucrose may be adjusted by the amount of methyl caprylate removed).

The reaction mixture is then cooled to 90° C. and neutralized with glacial acetic acid.

The product is diluted with hexane and the hexane solution washed several times with hot water.

The water washes are separated and the hexane, along with any residual water, is removed via $N_2$ sparging at 110° C. The product is then rediluted with hexane and is decolorized with a mixture of charcoal and filtrol.

The charcoal/filtrol is removed by vacuum filtration and the solvent removed by vacuum distillation. Excess and/or residual methyl esters are removed by thin film evaporation and the product crystallized from a hexane/methanol solution.

(Steam stripping at 210° C. and 1 mm Hg is an optional final step.)

EXAMPLE III

Preparation of a Reduced Calorie Shortening from a Compound of Example I and a Liquid Triglyceride Six grams of a solid $C_8$–$C_{22}$ sucrose polyester, prepared as in Example I, and 24 grams of Crisco Oil* are weighed into a sample vial. The mixture is heated on a steam bath and mixed by shaking. The mixture is then allowed to cool back to room temperature to form the plastic gel consisting of 20% of the sucrose polyester and 80% triglyceride oil.

*A liquid triglyceride oil marketed by The Procter & Gamble Company.

The shortening composition can be treated in the conventional manner with air or nitrogen to form an "aerated" shortening.

EXAMPLE IV

Preparation of Nondigestible Shortening from a Compound of Example I and a Liquid Sucrose Polyester Procedure:

Six grams of a solid $C_8$–$C_{22}$ sucrose polyester prepared as in Example I, and 24 grams of a liquid sucrose polyester are combined and heated until all solids are dissolved. The mixture is allowed to cool back to room temperature to form a plastic gel consisting of 20% solid sucrose polyester of Example I and 80% liquid sucrose polyester. The composition is suitable for use as a food fat and does not produce the anal leakage problem which would otherwise result if only the liquid sucrose polyester is used as a food fat.

The shortening composition can be treated in the conventional manner with air or nitrogen to form an "aerated" shortening.

EXAMPLE V

Preparation of Pentabehenyl Trilauryl Sucrose (Modified Methyl Ester Route)

In this Example 3 $C_{12}$/5 $C_{22}$ sucrose polyester is prepared by a modification of the methyl ester process described in Example II.

| Chemicals: | Mol. Wt. | Wt. (g) | Moles | Ratio |
|---|---|---|---|---|
| A. Reaction | | | | |
| 1. Sucrose | 342 | 68.4 | 0.20 | 1.000 |
| 2. Potassium Stearate | 322 | 48.3 | 0.15 | 0.750 |
| 3. Methyl Laurate | 214 | 192.6 | 0.90 | 4.500 |
| 4. Methyl Behenate | 354 | 531.0 | 1.50 | 7.500 |
| 5. Potassium Carbonate | 138 | 5.52 | 0.04 | 0.200 |
| B. Solvents | | | | |
| 1. Methanol | | | | |

Procedures:

Step A—Preparation of Potassium Stearate 44.8 grams of methyl stearate (0.75 moles/mole of sucrose to be used in Step B) is saponified by stirring at reflux in 200 ml methanol containing an equivalent amount of KOH (9.4 grams of 90% purity). The reaction is stirred at 60° C. for about an hour with heating until all methyl ester has been converted to soap as indicated by infrared analysis. The soap solution is used, as is, in the next reaction step.

Step B—Preparation of Lower Sucrose Esters 354 grams of methyl behenate (5 moles/mole of sucrose) is added directly to the potassium stearate-methyl alcohol solution from Step A above. 68.4 grams of sucrose 9anhydrous) and 2.76 grams potassium carbonate are then added to the soap-methyl behenate mixture. The reaction mixture is then heated to 135° C. to remove the methanol.

When the temperature reaches 135° C., the reaction mixture is placed under vacuum (about 2 mmHg). The reaction is allowed to proceed for about 1.5 hours until the sucrose is converted to its lower sucrose esters.

Step C—Preparation of $C_{12}$–$C_{22}$ Sucrose Polyesters

The lower sucrose esters crude (from Step B above), 177 gram of methyl behenate, and 192.6 grams of methyl laurate are combined with 2.76 grams of potassium carbonate in a reactor. While stirring, the temperature is dropped to 120° C. and the reactor placed under vacuum. The reflux is maintained to keep methyl laurate in the reactor by adjusting pressure with a nitrogen release valve. The reaction is allowed to proceed until the desired end point. The end point is determined by HPLC (High Pressure Liquid Chromatography).

Step D—Finished Process of $C_{12}$–$C_{22}$ Sucrose Polyesters

The reaction mixture is cooled to 90° C. and 20 ml of $H_2O$ is added to form the hydrate of the soap. The soap separates as a sludge and is removed by centrifugation.

The crude 5 $C_{22}$/3 $C_{12}$ sucrose is then decolorized with a mixture (2% by weight) of filtrol and celite. The mixture is stirred at 60° C. with nitrogen sparge for 30 minutes and the bleaching earths removed by vacuum filtration. Excess and/or residual methyl esters are removed by thin film evaporation at 240° C., 0.2 mmmHg. The product is then steam stripped at 210° C. and 1 mmHg for 3 hours to get the final product.

Yield-66% of theoretical.

Analytical:

1. % Octaester (HPLC)-89.5 2. Average degree of esterification-7.89 (calculated from % Octaester value as an approximation).

What is claimed is:

1. A fatty acid ester of sucrose, the fatty acid groups consisting essentially of short chain saturated straight chain fatty acid radicals containing from about 4 to about 12 carbon atoms and long chain saturated straight chain fatty acid radicals containing from about 20 to about 24 carbon atoms, the molar ratio of short chain to long chain radicals being from about 2:6 to 4:4, the degree of esterification being from about 7 to about 8 and the melting point being at least 47° C., provided however, when the short chain radical is $C_{12}$ the long chain radical is $C_{22}$.

2. The compound of claim 1 wherein the short chain acid radicals contain from about 6 to about 12 carbon atoms.

3. The compound of claim 1 wherein the short chain acid radicals contain from 6 to 10 carbon atoms.

4. The compound of claim 1 wherein the long chain acid radical is behenate.

5. The compound of claim 1 wherein the short chain acid radical is butyrate and the long chain acid radical is behenate.

6. The compound of claim 1 wherein the short chain acid radical is caproate and the long chain acid radical is behenate.

7. The compound of claim 1 wherein the short chain acid radical is caprylate and the long chain acid radical is behenate.

8. The compound of claim 1 wherein the short chain acid radical is caprate and the long chain acid radical is behenate.

9. The compound of claim 1 wherein the short chain radical is laurate and the long chain radical is behenate.

10. The compound as in any one of claims 1 or 2 through 9 wherein the molar ratio of short chain acid radical to long chain acid radical is from about 3:5 to 4:4.

11. The compound as in any one of claims 1 or 2 through 9 wherein the molar ratio of short chain acid radical to long chain acid radical is about 3:5.

12. A food composition comprising:

a) A nondigestible oil having a melting point below 37° C., and b) A fatty acid ester of sucrose, the fatty acid groups consisting essentially of short chain saturated straight chain fatty acid radicals containing from about 2 to about 12 carbon atoms and long chain saturated straight chain fatty acid radicals containing from about 20 to about 24 carbon atoms, the molar ratio of short chain to long chain radicals being from about 2:6 to 4:4, the degree of esterification being from about 7 to about 8 and the melting point being at least 47° C., provided however, when the short chain radical is $C_{12}$ the long chain radical is $C_{22}$;

wherein the weight ratio of a) to b) in said composition is from 9:1 to 4:1 so as to prevent the anal leakage problem associated with the ingestion of the nondigestible oil.

13. The composition of claim 12 wherein the short chain acid radicals of b) contain from about 6 to about 12 carbon atoms.

14. The composition of claim 12 wherein the short chain acid radicals of b) contain from 6 to 10 carbon atoms.

15. The composition of claim 12 wherein the long chain acid radical is b) is behenate.

16. The composition of claim 12 wherein the short chain acid radical of b) is butyrate and the long chain acid radical is behenate.

17. The composition of claim 12 wherein the short chain acid radical of b) is caproate and the long chain acid radical is behenate.

18. The composition of claim 12 wherein the short chain acid radical of b) is caprylate and the long chain acid radical is behenate.

19. The composition of claim 12 wherein the short chain acid radical of b) is caprate and the long chain acid radical is behenate.

20. The composition of claim 12 wherein the short chain radical of b) is laurate and the long chain radical is behenate.

21. The composition of claim 12 wherein the molar ratio of short chain to long chain acid radicals in b) is from about 3:5 to about 4:4.

22. The composition of any one of claims 12 through 21 wherein a) is a polyol fatty acid polyester having at least 4 fatty acid ester groups wherein the polyol is selected from the groups consisting of sugar and sugar alcohols containing from 4 to 8 hydroxyl group and wherein each fatty acid group has from about 8 to about 22 carbon atoms.

23. The composition of claim 22 wherein a) is a polyester of sucrose.

* * * * *